United States Patent
Ogo et al.

(10) Patent No.: US 7,479,570 B2
(45) Date of Patent: Jan. 20, 2009

(54) PROCESS FOR REDUCTION OF CARBON DIOXIDE WITH ORGANOMETALLIC COMPLEX

(75) Inventors: Seiji Ogo, Fukuoka (JP); Shuichi Fukuzumi, Mino (JP)

(73) Assignee: Japan Science and Technology Agency, Saitama (JP)

( * ) Notice: Subject to any disclaimer, the term of this patent is extended or adjusted under 35 U.S.C. 154(b) by 331 days.

(21) Appl. No.: 10/572,376

(22) PCT Filed: Sep. 10, 2004

(86) PCT No.: PCT/JP2004/013245

§ 371 (c)(1),
(2), (4) Date: Mar. 16, 2006

(87) PCT Pub. No.: WO2005/028408

PCT Pub. Date: Mar. 31, 2005

(65) Prior Publication Data

US 2007/0036706 A1  Feb. 15, 2007

(30) Foreign Application Priority Data

Sep. 17, 2003 (JP) ............................. 2003-324538

(51) Int. Cl.
*C07C 53/00* (2006.01)
(52) U.S. Cl. .................................................. 562/609
(58) Field of Classification Search ............... None
See application file for complete search history.

(56) References Cited

FOREIGN PATENT DOCUMENTS

| JP | 56-166146 | 12/1981 |
| JP | 59-112938 | 6/1984 |
| JP | 60-025948 | 2/1985 |
| JP | 2004-217632 | 8/2004 |
| JP | 2004-224715 | 8/2004 |

(Continued)

OTHER PUBLICATIONS

Hideki Hayashi, et al. (XP-002408247), "Accelerating Effect of a Proton on the Reduction of $CO_2$ Dissolved in Water under Acidic Conditions, Isolation, Crystal Structure, and Reducing Ability of a Water-Soluble Ruthenium Hydride Complex", *Journal of the American Chemical Society*, 2003, 125, pp. 14266-14267.

(Continued)

*Primary Examiner*—Karl J Puttlitz
(74) *Attorney, Agent, or Firm*—Harness, Dickey & Pierce, P.L.C.

(57) ABSTRACT

Carbon dioxide and water are mixed with an organometallic complex represented by general formula (1) below

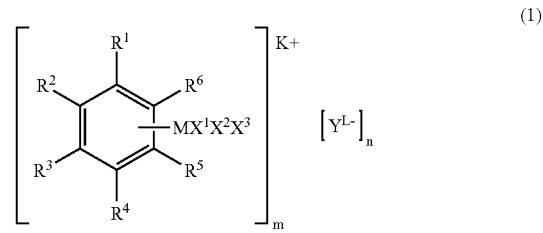

(1)

where $R^1$, $R^2$, $R^3$, $R^4$, $R^5$, and $R^6$ independently represent a hydrogen atom or a lower alkyl group, M represents an element that can be coordinated to the benzene ring, $X^1$ and $X^2$ represent nitrogen-containing ligands, $X^3$ represents a hydrogen atom, a carboxylic acid residue, or $H_2O$, $X^1$ and $X^2$ may be bonded to each other, Y represents an anion species, K represents a valency of a cation species, L represents a valency of an anion species, K and L independently represent 1 or 2, and K, m, L, and n are related to one another by K×m=L×n. This makes it possible to directly reduce carbon dioxide in water.

24 Claims, 1 Drawing Sheet

FOREIGN PATENT DOCUMENTS

| | | | |
|---|---|---|---|
| JP | 2004217632 | * | 8/2004 |
| JP | 2004224715 | * | 8/2004 |

OTHER PUBLICATIONS

Supplemental European Search Report dated Dec. 5, 2006.

G. Laurenczy et al., "Formation and Characterization of Water-Soluble Hydrido-Ruthenium (II) Complexes of 1,3,5-Triaza-7-phosphaadamantane and Their Catalytic Activity in Hydrogenation of $CO_2$ and $HCO_3$ in Aqueous Solution", *Inorganic Chemistry 2000*, vol. 39, No. 22, pp. 5083-5088.

Seiji Ogo et al., "pH-Dependent Transfer Hydrogenation of Ketones with HCOONa as a Hydrogen Donor Promoted by $(\eta^6-C_6Me_6)$Ru Complexes", *Organometallics 2002*, vol. 21, pp. 2964-2969.

* cited by examiner

PROCESS FOR REDUCTION OF CARBON DIOXIDE WITH ORGANOMETALLIC COMPLEX

TECHNICAL FIELD

The present invention relates to a reducing process of carbon dioxide with an organometallic complex, and in particular, relates to a reducing process of carbon dioxide in water under mild conditions.

BACKGROUND ART

Conventionally, reduction of carbon dioxide has been performed in toxic and exhaustible-resource-derived organic solvents. Recently, from the point of view of solving environmental and energy problems, reduction of carbon dioxide in water, which is non-toxic and low-cost, has been attempted. Reduction of hydrogen carbonate ion in water at pH 6 or above using an organometallic complex has been reported (for example, see Non-patent document 1), but no report has been made on reduction of carbon dioxide performed in water using an organometallic complex.

[Non-patent Document 1]

G. Laurenczy et al., Inorg. Chem., 2000, 39, pp. 5083-5088.

The present invention relates to a reaction of carbon dioxide in a water solvent or a mixed solvent of water and organic solvent, using an organometallic complex. If carbon dioxide ($CO_2$), instead of hydrogen carbonate ion ($HCO_3^-$), can be directly reduced by simply controlling the pH of water or a water-containing solvent, reaction can be easily controlled. This is beneficial as a reaction that is both economical and environmentally friendly.

In other words, the present invention has as an object to realize a reducing process of carbon dioxide in water, which is non-toxic and low-cost, (under mild conditions), using an organometallic complex.

DISCLOSURE OF INVENTION

After having diligently studied, the inventors of the present invention found that carbon dioxide can be reduced in water using an organometallic complex represented by general formula (1) below. The present invention showed for the first time that carbon dioxide could be reduced under mild conditions not in a toxic and exhaustible-resource-derived organic solvent but in water, which is non-toxic and low-cost, by using an organometallic complex.

A reducing process of carbon dioxide of the present invention is characterized in that the reducing process of carbon dioxide includes mixing carbon dioxide and water with an organometallic complex represented by general formula (1)

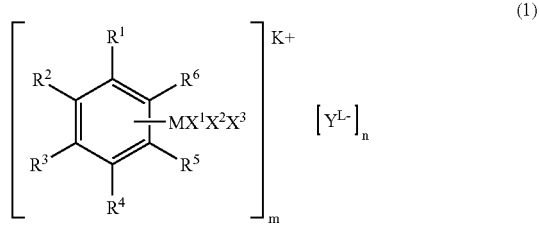

(1)

where $R^1$, $R^2$, $R^3$, $R^4$, $R^5$, and $R^6$ independently represent a hydrogen atom or a lower alkyl group, M represents an element that can be coordinated to the benzene ring, $X^1$ and $X^2$ represent nitrogen-containing ligands, $X^3$ represents a hydrogen atom, a carboxylic acid residue, or $H_2O$, $X^1$ and $X^2$ may be bonded to each other, Y represents an anion species, K represents a valency of a cation species, L represents a valency of an anion species, K and L independently represent 1 or 2, and K, m, L, and n are related to one another by $K \times m = L \times n$.

It is preferable that, in the organometallic complex represented by general formula (1), M represent a group 8 element or a group 9 element of the periodic table. It is further preferable that M be Ru.

Further, it is preferable that, in the organometallic complex represented by general formula (1), Y be one of a formate ion, a halide ion, a triflate ion, a sulfate ion, a perhalogen acid ion, a tetrafluoroborate ion, a hexafluorophosphoric acid ion, and a thiocyanic acid ion.

It is preferable that, in a reducing process of carbon dioxide of the present invention, a pH of a reaction system mixing the organometallic complex, carbon dioxide, and water be 6 or below. Further, when reducing the carbon dioxide by mixing the organometallic complex, carbon dioxide and a solvent containing water, the pH of the reaction system may be changed.

Additional objects, features, and strengths of the present invention will be made clear by the description below. Further, the advantages of the present invention will be evident from the following explanation in reference to the drawings.

BEST MODE FOR CARRYING OUT THE INVENTION

Figure 1A:
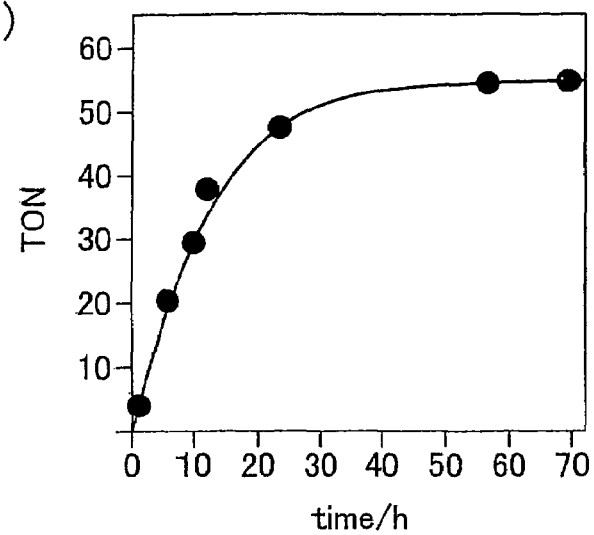
FIG. 1a illustrates that, with respect to formation of formic acid under a condition where a reaction temperature is at 40° C., a pressure of hydrogen is at 5.5 Mpa, and a pressure of carbon dioxide is at 2.5 Mpa by reducing carbon dioxide in water catalyzed with hydrido-4,4'-dimethoxy-2,2'-bipyridyl [(1,2,3,4,5,6-$\eta^6$)-hexamethylbenzene-1-yl]ruthenium(II) sulfate, a turnover number of reaction of the formation depends upon a reaction time.

The following describes the present invention in more detail, based on Examples and Comparative Examples. However, the present invention is not to be limited by the description below.

In a reducing process of carbon dioxide of the present invention, carbon dioxide is reduced by the reaction between the organometallic complex represented by general formula (1) above (hereinafter, simply referred to as "organometallic complex"), carbon dioxide, and water.

In the organometallic complex, lower alkyl groups represented as $R^1$, $R^2$, $R^3$, $R^4$, $R^5$, and $R^6$ are alkyl groups with one to six carbon atoms. Examples thereof include a methyl group, an ethyl group, a propyl group, a butyl group, a pentyl group, a hexyl group, an isopropyl group, a t-butyl group, an isoamyl group, a cyclopentyl group, and a cyclohexyl group. Each of the $R^1$, $R^2$, $R^3$, $R^4$, $R^5$, and $R^6$ in the organometallic complex may be the same type as the others or different type from the others.

Further, in the organometallic complex, M simply needs to be an element that can be coordinated to the benzene ring and is not limited to a particular element. It is, however, preferable that M be Fe, Ru, Os of the group 8 elements, or Co, Rh, Ir of the group 9 elements. Among the group 8 and 9 elements of the periodic table, Ru and Ir are more preferable. Ru is particularly preferable. By using these preferred elements, M can be assuredly coordinated to the benzene ring.

Further, examples of nitrogen-containing ligands represented as $X^1$, $X^2$ in the organometallic complex include: pyrrole; pyridine; imidazole; N-methylimidazole; acetonitrile; ammonia; aniline; 1,2-ethandiamine; 1,2-diphenyl-1,2-ethandiamine; 1,2-cyclohexanediamine; 2,2'-bipyridine; 4,4'-dimethoxy-2,2'-bipyridine; and 1,10-phenanthroline. Among the nitrogen-containing ligands exemplified above, the bidentate ligand is more preferable, and 2,2'-bipyridine and a derivative thereof are even more preferable. The nitrogen-containing ligands represented as $X^1$, $X^2$ of the organometallic complex may be the same ligands or different ligands. Further, the nitrogen-containing ligands $X^1$, $X^2$ may be bonded or not bonded to each other.

Examples of the anion species represented as Y in the organometallic complex include: carboxyl ion, such as formate ion or acetate ion; sulfate ion; halide ion, such as, fluoride ion, chloride ion, bromide ion, or iodide ion; perhalogen acid ion, such as triflate ion, perchlorate ion, perbromate ion, periodate ion; tetrafluoroborate ion; hexafluorophosphoric acid ion; and thiocyanate ion. Among the anion species exemplified above, the formate ion, the halide ion, the triflate ion, the sulfate ion, the perhalogen acid ion, the tetrafluoroborate ion, the hexafluorophosphoric acid ion, and the thiocyanate ion are more preferable.

Further, the organometallic complex needs to be the complex as represented by the formula (1). Concrete examples thereof include:

hydrido-2,2'-bipyridyl[(1,2,3,4,5,6-$\eta^6$)-hexamethylbenzene-1-yl]ruthenium(II)hexafluorophosphate;
hydrido-4,4'-dimethoxy-2,2'-bipyridyl[(1,2,3,4,5,6-$\eta^6$)-hexamethylbenzene-1-yl]ruthenium(II)hexafluorophosphate;
aqua-2,2'-bipyridyl[(1,2,3,4,5,6-$\eta^6$)-hexamethylbenzene-1-yl]ruthenium(II)hexafluorophosphate;
aqua-4,4'-dimethoxy-2,2'-bipyridyl[(1,2,3,4,5,6-$\iota^6$)-hexamethylbenzene-1-yl]ruthenium(II)hexafluorophosphate;
formato-2,2'-bipyridyl[(1,2,3,4,5,6-$\eta^6$)-hexamethylbenzene-1-yl]ruthenium(II)hexafluorophosphate;
formato-4,4'-dimethoxy-2,2'-bipyridyl[(1,2,3,4,5,6-$\eta^6$)-hexamethylbenzene-1-yl]ruthenium(II)hexafluorophosphate;
hydrido-2,2'-bipyridyl[(1,2,3,4,5,6-$\eta^6$)-hexamethylbenzene-1-yl]ruthenium(II)tetrafluoroborate;
hydrido-4,4'-dimethoxy-2,2'-bipyridyl[(1,2,3,4,5,6-$\eta^6$)-hexamethylbenzene-1-yl]ruthenium(II)tetrafluoroborate;
aqua-2,2'-bipyridyl[(1,2,3,4,5,6-$\eta^6$)-hexamethylbenzene-1-yl]ruthenium(II) tetrafluoroborate;
aqua-4,4'-dimethoxy-2,2'-bipyridyl[(1,2,3,4,5,6-$\eta^6$)-hexamethylbenzene-1-yl]ruthenium(II)tetrafluoroborate;
formato-2,2'-bipyridyl[(1,2,3,4,5,6-$\eta^6$)-hexamethylbenzene-1-yl]ruthenium(II) tetrafluoroborate;
formato-4,4'-dimethoxy-2,2'-bipyridyl[(1,2,3,4,5,6-$\eta^6$)-hexamethylbenzene-1-yl]ruthenium(II)tetrafluoroborate;
hydrido-2,2'-bipyridyl[(1,2,3,4,5,6-$\eta^6$)-hexamethylbenzene-1-yl]ruthenium(II)sulfate;
hydrido-4,4'-dimethoxy-2,2'-bipyridyl[(1,2,3,4,5,6-$\eta^6$)-hexamethylbenzene-1-yl]ruthenium(II) sulfate;
aqua-2,2'-bipyridyl[(1,2,3,4,5,6-$\eta^6$)-hexamethylbenzene-1-yl]ruthenium(II) sulfate;
aqua-4,4'-dimethoxy-2,2'-bipyridyl[(1,2,3,4,5,6-$\eta^6$)-hexamethylbenzene-1-yl]ruthenium(II) sulfate;
formato-2,2'-bipyridyl[(1,2,3,4,5,6-$\eta^6$)-hexamethylbenzene-1-yl]ruthenium(II) sulfate;
formato-4,4'-dimethoxy-2,2'-bipyridyl[(1,2,3,4,5,6-$\eta^6$)-hexamethylbenzene-1-yl]ruthenium(II) sulfate;
hydrido-2,2'-bipyridyl[(1,2,3,4,5,6-$\eta^6$)-hexamethylbenzene-1-yl]ruthenium(II)formate;
hydrido-4,4'-dimethoxy-2,2'-bipyridyl[(1,2,3,4,5,6-$\eta^6$)-hexamethylbenzene-1-yl]ruthenium(II)formate;
aqua-2,2'-bipyridyl[(1,2,3,4,5,6-$\eta^6$)-hexamethylbenzene-1-yl]ruthenium(II)formate;
aqua-4,4'-dimethoxy-2,2'-bipyridyl[(1,2,3,4,5,6-$\eta^6$)-hexamethylbenzene-1-yl]ruthenium(II)formate;
formato-2,2'-bipyridyl[(1,2,3,4,5,6-$\eta^6$)-hexamethylbenzene-1-yl]ruthenium(II)formate;
formato-4,4'-dimethoxy-2,2'-bipyridyl[(1,2,3,4,5,6-$\eta^6$)-hexamethylbenzene-1-yl]ruthenium(II)formate;
hydrido-2,2'-bipyridyl[(1,2,3,4,5,6-$\eta^6$)-cymene-1-yl]ruthenium(II)hexafluorophosphate;
hydrido-4,4'-dimethoxy-2,2'-bipyridyl[(1,2,3,4,5,6-$\eta^6$)-cymene-1-yl]ruthenium(II)hexafluorophosphate;
aqua-2,2'-bipyridyl[(1,2,3,4,5,6-$\eta^6$)-cymene-1-yl]ruthenium(II)hexafluorophosphate;
aqua-4,4'-dimethoxy-2,2'-bipyridyl[(1,2,3,4,5,6-$\eta^6$)-cymene-1-yl]ruthenium(II)hexafluorophosphate;
formato-2,2'-bipyridyl[(1,2,3,4,5,6-$\eta^6$)-cymene-1-yl]ruthenium(II)hexafluorophosphate;
formato-4,4'-dimethoxy-2,2'-bipyridyl[(1,2,3,4,5,6-$\eta^6$)-cymene-1-yl]ruthenium(II)hexafluorophosphate;
hydrido-2,2'-bipyridyl[(1,2,3,4,5,6-$\eta^6$)-cymene-1-yl]ruthenium(II)sulfate;
hydrido-4,4'-dimethoxy-2,2'-bipyridyl[(1,2,3,4,5,6-$\eta^6$)-cymene-1-yl]ruthenium(II)sulfate;
aqua-2,2'-bipyridyl[(1,2,3,4,5,6-$\eta^6$)-cymene-1-yl]ruthenium(II)sulfate;
aqua-4,4'-dimethoxy-2,2'-bipyridyl[(1,2,3,4,5,6-$\eta^6$)-cymene-1-yl]ruthenium(II)sulfate;
formato-2,2'-bipyridyl[(1,2,3,4,5,6-$\eta^6$)-cymene-1-yl]ruthenium(II)sulfate;
formato-4,4'-dimethoxy-2,2'-bipyridyl[(1,2,3,4,5,6-$\eta^6$)-cymene-1-yl]ruthenium(II)sulfate;
hydrido-2,2'-bipyridyl[(1,2,3,4,5,6-$\eta^6$)-cymene-1-yl]ruthenium(II)formate;
hydrido-4,4'-dimethoxy-2,2'-bipyridyl[(1,2,3,4,5,6-$\eta^6$)-cymene-1-yl]ruthenium(II)formate;
aqua-2,2'-bipyridyl[(1,2,3,4,5,6-$\eta^6$)-cymene-1-yl]ruthenium(II)formate;
aqua-4,4'-dimethoxy-2,2'-bipyridyl[(1,2,3,4,5,6-$\eta^6$)-cymene-1-yl]ruthenium(II)formate;
formato-2,2'-bipyridyl[(1,2,3,4,5,6-$\eta^{16}$)-cymene-1-yl]ruthenium(II)formate;
formato-4,4'-dimethoxy-2,2'-bipyridyl[(1,2,3,4,5,6-$\eta^{16}$)-cymene-1-yl]ruthenium(II)formate;
hydrido-2,2'-bipyridyl[(1,2,3,4,5,6-$\eta^6$)-cymene-1-yl]ruthenium(II)tetrafluoroborate;
hydrido-4,4'-dimethoxy-2,2'-bipyridyl[(1,2,3,4,5,6-$\eta^6$)-cymene-1-yl]ruthenium(II)tetrafluoroborate;
aqua-2,2'-bipyridyl[(1,2,3,4,5,6-$\eta^6$)-cymene-1-yl]ruthenium(II)tetrafluoroborate;
aqua-4,4'-dimethoxy-2,2'-bipyridyl[(1,2,3,4,5,6-$\eta^6$)-cymene-1-yl]ruthenium(II)tetrafluoroborate;

formato-2,2'-bipyridyl[(1,2,3,4,5,6-η⁶)-cymene-1-yl]ruthenium(II)tetrafluoroborate;

formato-4,4'-dimethoxy-2,2'-bipyridyl[(1,2,3,4,5,6-η⁶)-cymene-1-yl]ruthenium(II)tetrafluoroborate. Among the compound exemplified above, preferred compounds include:

aqua-2,2'-bipyridyl[(1,2,3,4,5,6-η⁶)-hexamethylbenzene-1-yl]ruthenium(II)sulfate;

formato-2,2'-bipyridyl[(1,2,3,4,5,6-η⁶)-hexamethylbenzene-1-yl]ruthenium (II)formate;

hydrido-2,2'-bipyridyl[(1,2,3,4,5,6-η⁶)-hexamethylbenzene-1-yl]ruthenium(II)hexafluorophosphoric acid; and hydrido-4,4'-dimethoxy-2,2'-bipyridyl[(1,2,3,4,5,6-η⁶)-hexamethylbenzene-1-yl]ruthenium(II)sulfate.

The organometallic complex can be produced in accordance with, for example, Organometalics 2002, 21, pp. 2964-2969 (authors: Seiji Ogo, Tsutomu Abura, and Yoshihito Watanabe). The following more concretely describes an exemplary method of production.

(Process of Producing Organometallic Complex)

(1) In the presence of water at pH 3.8, triaqua[(1,2,3,4,5,6-η⁶)-hexamethylbenzene-1-yl]ruthenium(II) sulfate is reacted with 2,2'-bipyridine to produce aqua-2,2'-bipyridyl[(1,2,3,4,5,6-η⁶)-hexamethylbenzene-1-yl]ruthenium(II) sulfate. Under the same conditions, triaqua[(1,2,3,4,5,6-η⁶)-hexamethylbenzene-1-yl]ruthenium(II) sulfate is reacted with 4,4'-dimethoxy-2,2'-bipyridine to produce aqua-4,4'-dimethoxy-2,2'-bipyridyl[(1,2,3,4,5,6-η⁶)-hexamethylbenzene-1-yl]ruthenium(II)sulfate.

(2) In the presence of water at pH 4.0, the aqua-2,2'-bipyridyl[(1,2,3,4,5,6-η¹⁶)-hexamethylbenzene-1-yl]ruthenium(II) sulfate obtained in the way described above is reacted with sodium formate to produce formato-2,2'-bipyridyl[(1,2,3,4,5,6-η⁶)-hexamethylbenzene-1-yl]ruthenium(II)formate. Under the same conditions, aqua-4,4'-dimethoxy-2,2'-bipyridyl[(1,2,3,4,5,6-η⁶)-hexamethylbenzene-1-yl]ruthenium(II)sulfate is reacted with sodium formate to produce formato-4,4'-dimethoxy-2,2'-bipyridyl[(1,2,3,4,5,6-η⁶)-hexamethylbenzene-1-yl]ruthenium(II)formate.

Further, in the presence of water at pH 8.0, the aqua-2,2'-bipyridyl[(1,2,3,4,5,6-η⁶)-hexamethylbenzene-1-yl]ruthenium(II)sulfate obtained in the way described above is reacted with sodium formate and then with sodium hexafluorophosphate to produce hydrido-2,2'-bipyridyl[(1,2,3,4,5,6-η⁶)-hexamethylbenzene-1-yl]ruthenium(II)hexafluorophosphate. Further, aqua-4,4'-dimethoxy-2,2'-bipyridyl[(1,2,3,4,5,6-η⁶)-hexamethylbenzene-1-yl]ruthenium(II)sulfuric acid is reacted with sodium formate and then with sodium hexafluorophosphate to produce hydrido-4,4'-dimethoxy-2,2'-bipyridyl[(1,2,3,4,5,6-η⁶)-hexamethylbenzene-1-yl]ruthenium(II)hexafluorophosphate.

(3) For the reactions described above in (2), an inert organic solvent may be used. In other words, the reaction may be performed in a mixed water-containing solvent of a predetermined pH and organic solvent that is inert to the reaction. Concrete examples of such organic solvent include hydrocarbon, halogenated hydrocarbon, ether, and ester. Further concrete examples thereof include toluene, hexane, chloroform, chlorobenzene, diethylether, t-butylmethylether, and ethyl acetate.

(4) The reaction described above in (2) is normally performed at a reaction temperature of −40° C. to 200° C. It is preferable that the reaction be performed at a reaction temperature of −20° C. to 100° C. Further, the reaction described in (2) is normally completed within several hours to approximately 30 hours, depending upon the conditions of reaction (for example, concentration of reacting substrate, or reaction temperature). By using the organometallic complex represented by general formula (1), carbon dioxide can be reduced more efficiently in water under mild conditions.

By reducing carbon dioxide using the reducing process of the embodiment, formic acid or alikali salt thereof can be obtained. In other words, the reducing process of carbon dioxide of the embodiment allows carbon dioxide in a water-containing solution to be reduced so as to produce formic acid or alikali salt thereof. Examples of the alikali constituting an alikali salt of the formic acid include alkali metals and alkaline-earth metals. Among the alikalis exemplified above, sodium and potassium are preferable. In other words, it is preferable that the reducing process of carbon dioxide of the embodiment be performed under such conditions that a sodium salt or a potassium salt of formic acid is obtained as a consequence of the reduction of carbon dioxide.

A quantity of the organometallic complex used in the reduction of the present invention is not limited to a particular quantity. The organometallic complex, however, is normally used at a mole ratio of about 1 to 1/100,000 with respect to the carbon dioxide used as a reacting substrate (carbon dioxide/organometallic complex). A mole ratio of about 1/50 to 1/10,000 is more preferable.

Further, in a case where formic acid or a salt thereof is used for preparing an organometallic complex represented by general formula (1), the quantity of organometallic complex is not limited to a particular quantity as long as the quantity is equivalent to or greater than the carbon dioxide used as a reacting substrate. It is, however, preferable that the quantity fall in a range of 1 to 100 equivalents.

In a reducing process of the embodiment, the process of mixing the organometallic complex, carbon dioxide, and water is not particularly limited. Concrete examples of the process include: (1) a process in which a water-containing solution dissolving carbon dioxide is mixed with the organometallic complex; (2) a process in which an aqueous solution dissolving the organometallic complex is mixed with gaseous carbon dioxide; and (3) a process in which an aqueous solution dissolving carbon dioxide is mixed with a liquid containing the organometallic complex.

The reducing process of carbon dioxide of the embodiment can be performed either in the presence or in the absence of a solvent that is inert to the reaction of carbon dioxide. Examples of the solvent used in the reducing process of the embodiment include water (aqueous solvent) or a mixed solvent of water and solvent other than water. The mixed solvent may be a mixed solvent of water and organic solvent miscible to water. Further, the mixed solvent may be a mixed solvent of water and organic solvent immiscible to water (two-phase solvent).

Examples of solvents other than water include: a solvent of ether, such as dimethoxyethan or tetrahydrofuran; a solvent of aliphatichydrocarbon, such as hexane, cyclohexane, or heptane; a solvent of aromatic hydrocarbon, such as benzene, toluene, or xylene; an inert solvent of fluorine, such as Fluorinert™ FC-40, FC-43, FC-70, FC-72, or FC-75; a solvent of aromatic hydrocarbon halide, such as chlorobenzene or dichlorobenzene; and a mixture of the compounds exemplified above as the solvents.

In the water-containing solvent, carbon dioxide and water exhibit the chemical equilibrium represented by formula (2) below (reaction on the left-hand side: $pK_1$=6.35, reaction on the right-hand side: $pK_2$=10.33).

$$CO_2 + H_2O \leftrightarrows HCO_3^- + H^+ \leftrightarrows CO_3^{2-} + 2H^+ \tag{2}$$

Because the reaction equilibrium between carbon dioxide and water in the water-containing solvent satisfies the relationship set forth in the formula (2), it is preferable that the pH of the reaction system in the reducing process of the embodiment described above fall in a range of 1 to 10. It is more preferable that the pH fall in a range of 1 to 6. Further, in the reducing process of carbon dioxide of the embodiment, hydrogen ion ($H^+$) serves as a catalyst (acid catalyst) for accelerating the reduction reaction. Therefore, by setting the pH of the reaction system at 6 or below, the reduction reaction can be accelerated. Further, in order to accelerate the reduction reaction catalyzed by the hydrogen ion, it is preferable that the pH of the reaction system fall in a range of 3 to 5 in particular. The lower limit of the pH is not limited to a particular pH, and the pH can be set based upon stability of the organometallic complex or a speed of the intended reduction reaction.

In the reducing process of the embodiment, when reducing the carbon dioxide by mixing the organometallic complex, carbon dioxide, and water, the pH of the reaction system may be changed. In this way, the reaction equilibrium between carbon dioxide and water in the reaction system can be shifted to change the quantity of carbon dioxide. Further, the acid catalytic effect of the hydrogen ion can be changed as well. Therefore, for example, the rate of the reduction reaction of carbon dioxide can be controlled.

The active species of catalyzing the reduction of the organometallic complex is an organometallic complex (hydride complex) as represented by general formula (1), where $X^3$ is a hydrogen atom. The hydride complex itself can be efficiently produced by, for example, reacting $(1,2,3,4,5,6-\eta^6)$-hexamethylbenzene-1-yl]ruthenium(II) sulfate with formic acid or a salt thereof in a pH range of 4 or above, or more preferably in a pH range of 4 to 10. The reaction of the formic acid or a salt thereof is carried out under the reaction conditions of the reducing process of carbon dioxide of the embodiment. Further, the hydride complex can be directly used as a reducing agent of carbon dioxide.

In the reducing process of carbon dioxide of the embodiment, the reaction of the organometallic complex, carbon dioxide, and water is normally performed in a temperature range of −90° C. to 200° C., or more preferably −20° C. to 100° C. The reaction time of the reduction reaction of carbon dioxide varies depending upon reaction conditions such as the concentration of the carbon dioxide used as a reacting substrate, the reaction temperature, the amount of the organometallic complex, and the type of solvent other than water. Normally, the reaction time is approximately several minutes to 24 hours. In other words, the reduction reaction of carbon dioxide is completed within several minutes to 24 hours.

A method for isolating and purifying a target product of the reduction reaction of carbon dioxide is not limited to a particular method, and publicly-known methods can be used therefor. For example, after the reaction is completed, a solvent and materials that did not react are removed, and, if necessary, the target product is water-washed or distilled. Further, the organometallic complex may be removed from the target product by washing, distillation, adsorption, or other procedures. Further, the organometallic complex may be removed by filtration after the organometallic complex is held on an appropriate carrier, such as a silica gel or activated clay. The collected organometallic complex can be reused.

As described above, the reducing process of carbon dioxide of the embodiment uses an organometallic complex represented by general formula (1), and therefore allows carbon dioxide to be directly reduced not in a toxic and exhaustible-resource-derived organic solvent but in water, which is non-toxic and low-cost thereby solving environmental and energy problems.

The following describes the present invention in more detail based on Examples. However, the present invention is not to be limited by the description below.

EXAMPLE 1

Preparation of aqua-2,2'-bipyridyl[(1,2,3,4,5,6-$\eta^6$)-hexamethylbenzene-1-yl]ruthenium(II)sulfate 187 mg of 2,2'-bipyridine (1.2 mmol) was added to a 100 mL of aqueous solution containing 496 mg (1.2 mmol) of triaqua[(1,2,3,4,5,6-$\eta^6$)-hexamethylbenzene-1-yl]ruthenium (II)sulfate, and was stirred for 12 hours at room temperature. A resulting pale orange solution was concentrated. As a result, aqua-2,2'-bipyridyl[(1,2,3,4,5,6-$\eta^6$)-hexamethylbenzene-1-yl]ruthenium(II)sulfate was obtained as a yellow powder (yield: 90%). It was confirmed by $^1$H-NMR measurement that the obtained yellow powder was aqua-2,2'-bipyridyl[(1,2,3,4,5,6-$\eta^6$)-hexamethylbenzene-1-yl]ruthenium (II)sulfate. The following is the result of the measurement.

$^1$H-NMR($D_2O$ at pD 3.8, internal standard3-(trimethylsilyl)propionic acid-2,2,3,3-$d_4$sodium salt) δ: 2.13(s,18H), 7.88(t,2H), 8.20(t,2H), 8.40(d,2H), 9.16(d,2H).

EXAMPLE 2-1

Preparation of hydrido-2,2'-bipyridyl[(1,2,3,4,5,6-$\eta^6$)-hexamethylbenzene-1-yl]ruthenium(II)trifluoromethanesulfonic acid phosphate 4.0 mg (106 mmol) of solid boron sodium hydride was added at room temperature to an aqueous solution (10 mL) containing 48.0 mg (90.0 mmol) of aqua-2,2'-bipyridyl[(1,2,3,4,5,6-$\eta^6$)-hexamethylbenzene-1-yl]ruthenium(II)sulfate obtained by the preparation method described in Example 1. As a result, a small amount of black precipitate and orange solution were obtained. After the black precipitate was filtered out from the orange solution obtained as described above, 33 mg (0.192 mmol) of trifluoromethanesulfonic acid sodium was added to the orange solution, with the result that a precipitate was formed immediately. The precipitate was removed by filtration, washed with water, and then dried under reduced pressure. As a result, orange hydrido-2,2'-bipyridyl[(1,2,3,4,5,6-$\eta^6$)-hexamethylbenzene-1-yl]ruthenium(II)trifluoromethanesulfonate, which is an organometallic complex represented by general formula (1), was obtained (yield: 70%). It was confirmed by $^1$H-NMR measurement that the obtained substance was hydrido-2,2'-bipyridyl[(1,2,3,4,5,6-$\eta^6$)-hexamethylbenzene-1-yl]ruthenium(II)trifluoromethanesulfonate. The following is the result of the measurement.

$^1$H-NMR($D_2O$, internal standard3-(trimethylsilyl)propionic acid-2,2,3,3-$d_4$sodium salt) δ:2.14(s,18H), 7.48(t,2H), 7.93(t,2H), 8.19(d,2H), 8.57(d,2H), −7.45(s).

EXAMPLE 2-2

Preparation of hydrido-2,2'-bipyridyl[(1,2,3,4,5,6-$\eta^6$)-hexamethylbenzene-1-yl]ruthenium(II)hexafluorophosphate 53.3 mg (0.1 mmol) of aqua-2,2'-bipyridyl[(1,2,3,4,5,6-$\eta^6$)-hexamethylbenzene-1-yl]ruthenium(II)sulfate obtained by the preparation method described in Example 1, and 680 mg (10 mmol) of sodium formate were dissolved in 15 mL of water at room temperature. Then, 0.1 M sodium hydroxide was added to the solution to adjust the pH to 8.0. The solution then was stirred for 30 minutes at 70° C. Then, the solution was added to 4 mL of aqueous solution containing 16.8 mg (0.1 mmol) of sodium hexafluorophosphate maintained at room temperature. A resulting (deposited) crystal was filtered, and then washed and dried. As a result, hydrido-2,2'-bipyridyl[(1,2,3,4,5,6-$\eta^6$)-hexamethylbenzene-1-yl]ruthenium(II)hexafluorophosphate, which is an organometallic complex represented by general formula (1) was obtained (yield: 65%). It was confirmed by $^1$H-NMR measurement that the obtained substance was hydrido-2,2'-bipyridyl[(1,2,3,4,5,6-$\eta^6$)-hexamethylbenzene-1-yl]ruthenium(II)hexafluorophosphate. The following is the result of the measurement.

$^1$H-NMR(D$_2$O, internal standard3-(trimethylsilyl)propionic acid-2,2,3,3-d$_4$ sodium salt) δ: 2.14(s,18H), 7.48(t,2H), 7.93(t,2H), 8.19(d,2H), 8.57(d,2H), −7.45(s).

EXAMPLE 2-3

Preparation of hydrido-2,2'-bipyridyl[(1,2,3,4,5,6-$\eta^6$)-hexamethylbenzene-1-yl]ruthenium(II)sulfate Under argon atmosphere, 5.32 mg (9.97 mmol) of aqua-2,2'-bipyridyl[(1,2,3,4,5,6-$\eta^6$)-hexamethylbenzene-1-yl]ruthenium(II)sulfate obtained by the preparation method described Example 1, and 6.64 mg of (97.6 mmol) sodium formate were dissolved in water (1 mL) maintained at room temperature. Through argon, the resulting aqueous solution was stirred for 10 minutes at 70° C. As a result, an orange solution of hydrido-2,2'-bipyridyl[(1,2,3,4,5,6-$\eta^6$)-hexamethylbenzene-1-yl]ruthenium(II)sulfate, which is an organometallic complex represented by general formula (1) was obtained. It was confirmed by $^1$H-NMR measurement that the orange solution was hydrido-2,2'-bipyridyl[(1,2,3,4,5,6-$\eta^6$)-hexamethylbenzene-1-yl]ruthenium(II)sulfate. The following is the result of the measurement.

$^1$H-NMR(D$_2$O, internal standard3-(trimethylsilyl)propionic acid-2,2,3,3-d$_4$ sodium salt) δ: 2.14(s,18H), 7.48(t,2H), 7.93(t,2H), 8.19(d,2H), 8.57(d,2H), −7.45(s).

EXAMPLE 3

Preparation of formato-2,2'-bipyridyl[(1,2,3,4,5,6-$\eta^6$)-hexamethylbenzene-1-yl]ruthenium(II)formate At room temperature, 53.3 mg (0.1 mmol) of aqua-2,2'-bipyridyl[(1,2,3,4,5,6-$\eta^6$)-hexamethylbenzene-1-yl]ruthenium(II)sulfate obtained by the preparation method described in Example 1, and 2.72 g (40 mmol) of sodium formate were dissolved in 20 mL of water. Then, a 3M formic acid aqueous solution was added to the resulting aqueous solution to adjust the pH of the solution to 4.0. The adjusted aqueous solution was stirred for 30 minutes at 40° C. Then, 10 mL of chloroform was added to the aqueous solution, and the aqueous solution was extracted five times. The extract so obtained was dried with magnesium chloride and then concentrated. The resulting residue was dissolved in a mixed solvent of chloroform and diethylether, and then was recrystallized. As a result, formato-2,2'-bipyridyl[(1,2,3,4,5,6-$\eta^6$)-hexamethylbenzene-1-yl]ruthenium(II)formate, which is an organometallic complex represented by general formula (1) was obtained (yield: 50%). It was confirmed by $^1$H-NMR measurement that the obtained substance was formato-2,2'-bipyridyl[(1,2,3,4,5,6-$\eta^6$)-hexamethylbenzene-1-yl]ruthenium(II)formate. The following is the result of the measurement.

$^1$H-NMR(CDC13, internal standard tetrametylsilane) δ: 2.10(s,18H), 7.67(t,2H), 7.79(s,1H), 8.16(t,2H), 9.14(d,2H).

EXAMPLE 4

Reduction of Carbon Dioxide

Carbon dioxide at an atmospheric pressure 1 was passed through water for 0.30 minutes, so as to prepare an aqueous solution of saturated carbon dioxide at the pH 4.0. Then, 10.0 mg (17.6 mmol) of hydrido-2,2'-bipyridyl[(1,2,3,4,5,6-$\eta^6$)-hexamethylbenzene-1-yl]ruthenium(II)trifluoromethanesulfonate obtained by the preparation method described Example 2-1 and constitutes an organometallic complex represented by general formula (1) was added to the carbon dioxide aqueous solution (3 mL). Under carbon dioxide atmosphere, the solution was stirred for three hours at room temperature. As a result, formato-2,2'-bipyridyl[(1,2,3,4,5,6-$\eta^6$)-hexamethylbenzene-1-yl]ruthenium(II)trifluoromethanesulfonate, aqua-2,2'-bipyridyl[(1,2,3,4,5,6-$\eta^6$)-hexamethylbenzene-1-yl]ruthenium(II)trifluoromethanesulfonate, and formate ion were produced. Formation thereof was confirmed by $^1$H-NMR measurement. The following is the result of the measurement.

$^1$H-NMR(CDC13,internal standardtetrametylsilane) δ: 2.10(s,18H), 7.67(t,2H), 7.79(s,1H), 8.16(t,2H), 9.14(d,2H) of formato-2,2'-bipyridyl[(1,2,3,4,5,6-$\eta^6$)-hexamethylbenzene-1-yl]ruthenium(II)trifluoromethanesulfonate.

1H-NMR(D$_2$O at pD3.8,internal standard3-(trimethylsilyl)propionic acid-2,2,3,3-d$_4$ sodium salt) δ: 2.13(s,18H), 7.88(t,2H), 8.20(t,2H), 8.40(d,2H), 9.16(d,2H) of aqua-2,2'-bipyridyl[(1,2,3,4,5,6-$\eta^6$)-hexamethylbenzene-1-yl]ruthenium(II)trifluoromethanesulfonate.

As described in Examples, above by mixing hydrido-2,2'-bipyridyl[(1,2,3,4,5,6-$\eta^6$)-hexamethylbenzene-1-yl]ruthenium(II)trifluoromethanesulfonate(organometallic complex), carbon dioxide, and water, carbon dioxide was reduced and formate ion was produced.

EXAMPLE 5

Reduction of Carbon Dioxide Ultilizing aqua-4,4'-dimethoxy-2,2'-bipyridyl[(1,2,3,4,5,6-$\eta^6$)-hexamethylbenzene-1-yl]ruthenium(II)sulfate or hydrido-4,4'-dimethoxy-2,2'-bipyridyl-[(1,2,3,4,5,6-$\eta^6$)-hexamethylbenzene-1-yl]ruthenium(II)sulfate After 70 hours of reaction at 40° C., the turnover number (TONs) of the reduction reaction in water catalyzed by aqua-4,4'-dimethoxy-2,2'-bipyridyl[(1,2,3,4,5,6-$\eta^6$)-hexamethylbenzene-1-yl]ruthenium(II)sulfate was 55, whereas the turnover number of the reduction reaction in water catalyzed by aqua-2,2'-bipyridyl[(1,2,3,4,5,6-$\eta^6$)-hexamethylbenzene-1-yl]ruthenium(II)sulfate was 35.

In other words, by using aqua-4,4'-dimethoxy-2,2'-bipyridyl[(1,2,3,4,5,6-$\eta^6$)-hexamethylbenzene-1-yl]ruthenium(II)sulfate, the turnover number was increased significantly.

Therefore, it can be said that the reaction of Examples using aqua-4,4'-dimethoxy-2,2'-bipyridyl[(1,2,3,4,5,6-$\eta^6$)-hexamethylbenzene-1-yl]ruthenium(II)sulfate is industrially superior to the reaction using aqua-2,2'-bipyridyl[(1,2,3,4,5,6-$\eta^6$)-hexamethylbenzene-1-yl]ruthenium(II)sulfate.

Figure 1B:
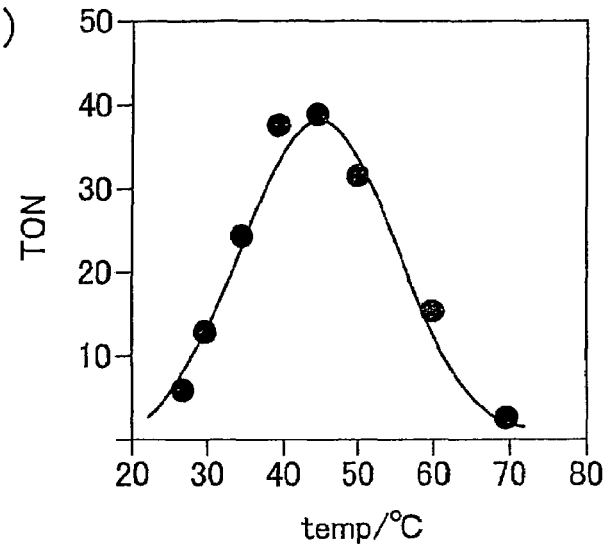
FIG. 1b illustrates a relationship between a turnover number and a reaction temperature 12 hours after the reaction started.
Figure 1C:
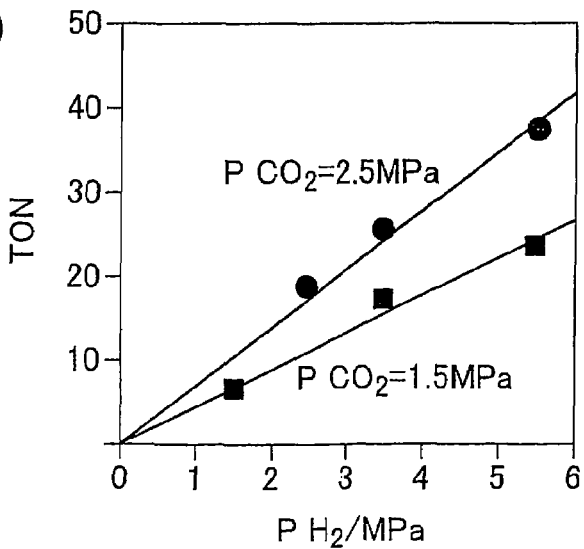
FIG. 1c illustrates dependence of a turnover number of reduction reaction of carbon dioxide performed in water upon a pressure of hydrogen, under a condition where the pressure of carbon dioxide is at 1.5 MPa or 2.5 MPa in a case where the water is catalyzed with hydrido-4,4'-dimethoxy-2,2'-bipyridyl[(1,2,3,4,5,6-$\eta^6$)-hexamethylbenzene-1-yl]ruthenium (II)sulfate and the reaction continued for 12 hours at 40° C.

Conditions of the catalytic reaction were optimized by the reaction time, the reaction temperature, and the pressure of hydrogen and the pressure of carbon dioxide. FIGS. 1a, 1b, and 1c show how the turnover number is related to the reaction time, the reaction temperature, and the pressures of hydrogen and carbon dioxide, respectively.

FIG. 1a shows reaction-time dependence of the turnover number of the formic acid forming reaction in which carbon dioxide is reduced in water by being catalyzed by hydrido-4,4'-dimethoxy-2,2'-bipyridyl[(1,2,3,4,5,6-η⁶)-hexamethylbenzene-1-yl]ruthenium(II)sulfate under the conditions where the reaction temperature is at 40° C., the pressure of hydrogen is at 5.5 Mpa, and the pressure of carbon dioxide is at 2.5 Mpa. The turnover number increased with time until the turnover number reached an equilibrium 55 hours after the start of reaction.

FIG. 1b shows a relationship between the turnover number and the reaction temperature 12 hours after the start of the reaction. The turnover number increased as the reaction temperature increased. The turnover number reached a maximum value at 40° C., decreased thereafter as the reaction temperature increased.

The reverse reaction of the reduction, that is, the reaction causing a decrease of the turnover number at high temperatures, as shown in FIG. 1b, was performed in water by reacting hydrido-4,4'-dimethoxy-2,2'-bipyridyl[(1,2,3,4,5,6-η⁶)-hexamethylbenzene-1-yl]ruthenium(II)sulfate with a 10 times or more amount of formic acid, under the conditions where the temperature was at 60° C. and the pH was at 2.4.

One hour after the start of the reaction, 90% or greater amount of the formic acid disappeared, and hydrogen and carbon dioxide were produced. This was confirmed by ¹H-NMR and gas chromatography.

On the other hand, 12 hours after the start of the reaction performed at the reaction temperature of 40° C., the turnover number was proportional to the increase of hydrogen pressure. The slope increased as the pressure of carbon dioxide increased. FIG. 1c shows hydrogen-pressure dependence of the turnover number of the reduction reaction of carbon dioxide performed in water at 40° C. for 12 hours and under the carbon dioxide pressures of 1.5 Mpa and 2.5 Mpa, and catalyzed by hydrido-4,4'-dimethoxy-2,2'-bipyridyl[(1,2,3,4,5,6-η⁶)-hexamethylbenzene-1-yl]ruthenium(II) sulfate.

As described above, the Examples showed that carbon dioxide can be reduced in water under acidic conditions if water-soluble aqua-4,4'-dimethoxy-2,2'-bipyridyl[(1,2,3,4,5,6-η⁶)-hexamethylbenzene-1-yl]ruthenium(II)sulfate or hydrido-4,4'-dimethoxy-2,2'-bipyridyl-[(1,2,3,4,5,6-η⁶)-hexamethylbenzene-1-yl]ruthenium(II)sulfate were used under optimized catalytic conditions.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

As described above, the reducing process of carbon dioxide of the present invention (hereinafter, this will be referred to as "reducing process of the present invention") is a process in which the organometallic complex represented by general formula (1) is mixed with carbon dioxide and water. With the organometallic complex represented by general formula (1), carbon dioxide can be reduced in water under mild conditions, not in an toxic and exhaustible-resource-derived organic solvent, thereby solving environmental and energy problems.

Further, it is preferable in the reducing process of the present invention that the pH of the reaction system mixing the organometallic complex, carbon dioxide, and water be 6 or below. The reduction reaction of the present invention is accelerated by an acid catalyst. Therefore, by adjusting the pH of the reaction system to 6 or below, efficiency of the reduction reaction can be improved. Further, at a pH of 6 or above, more than half of the carbon dioxide in the reaction system becomes hydrogencarbonate ion ($HCO_3^-$) by the reaction with water. On the other hand, at a pH of 6 or below, majority of the carbon dioxide exists as weakly hydrated carbon dioxide. Therefore, by adjusting the pH of the reaction system to 6 or below, the proportion of carbon dioxide in the reaction system can be increased, and the reduction reaction can be efficiently proceeded.

Further, in the reducing process of the present invention, when reducing the carbon dioxide by mixing the organometallic complex, carbon dioxide, and water, the pH of the reaction system may be changed. As described above, in the reducing process of the present invention, the rate of reduction reaction and the proportion of carbon dioxide contained in the reaction system can be controlled by changing the pH of the reaction system. In other words, by controlling the pH of the reaction system, the reduction reaction can be easily controlled.

Accordingly, the reducing process of carbon dioxide of the present invention enables carbon dioxide to be directly reduced not in a toxic and exhaustible-resource-derived organic solvent but in water, which is non-toxic and low-cost, thereby solving environmental and energy problems.

The invention claimed is:

1. A reducing process of carbon dioxide, comprising mixing carbon dioxide and water with an organometallic complex represented by general formula (1) so as to reduce carbon dioxide so that formic acid or alkali salt thereof is formed,

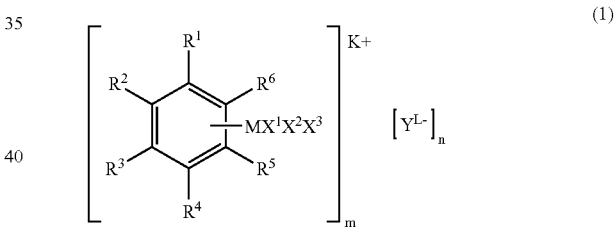

where $R^1$, $R^2$, $R^3$, $R^4$, $R^5$, and $R^6$ independently represent a hydrogen atom or a lower alkyl group, M represents an element that can be coordinated to the benzene ring, $X^1$ and $X^2$ represent nitrogen-containing ligands, $X^3$ represents a hydrogen atom, a carboxylic acid residue, or $H_2O$, $X^1$ and $X^2$ may be bonded to each other, Y represents an anion species, K represents a valency of a cation species, L represents a valency of an anion species, K and L independently represent 1 or 2, and K, m, L, and n are related to one another by K×m=L×n.

2. A reducing process of carbon dioxide as set forth in claim 1, wherein, in the organometallic complex represented by general formula (1), M represents a group 8 element or a group 9 element of the periodic table.

3. A reducing process of carbon dioxide as set forth in claim 2, wherein in the organometallic complex represented by general formula (1), M is Ru.

4. A reducing process of carbon dioxide as set forth in claim 1, wherein, in the organometallic complex represented by general formula (1), Y is one of a formate ion, a halide ion, a triflate ion, a sulfate ion, a perhalogen acid ion, a tetrafluoroborate ion, a hexafluorophosphoric acid ion, and a thiocyanate ion.

5. A reducing process of carbon dioxide as set forth claim 1, wherein, in the organometallic complex represented by general formula (1), the nitrogen-containing ligands represented by $X^1$ and $X^2$ are 4,4'-dimethoxy-2,2'-bipyridine.

6. A reducing process of carbon dioxide as set forth in claim 1, wherein a pH of a reaction system mixing the organometallic complex, carbon dioxide, and water is 6 or below.

7. A reducing process of carbon dioxide as set forth in claim 1, wherein, when reducing the carbon dioxide by mixing the organometallic complex, carbon dioxide, and water, the pH of the reaction system is changed.

8. A reducing process of carbon dioxide as set forth in claim 5, comprising the steps of:
   adding hydrogen to a reaction system mixing the organometallic complex of general formula (1), carbon dioxide, and water, where the nitrogen-containing ligands represented by $X^1$ and $X^2$ are 4,4'-dimethoxy-2,2'-bipyridine; and
   applying a pressure on the reaction system.

9. A reducing process of carbon dioxide as set forth in claim 2, wherein, in the organometallic complex represented by general formula (1), Y is one of a formate ion, a halide ion, a triflate ion, a sulfate ion, a perhalogen acid ion, a tetrafluoroborate ion, a hexafluorophosphoric acid ion, and a thiocyanate ion.

10. A reducing process of carbon dioxide as set forth in claim 3, wherein, in the organometallic complex represented by general formula (1), Y is one of a formate ion, a halide ion, a triflate ion, a sulfate ion, a perhalogen acid ion, a tetrafluoroborate ion, a hexafluorophosphoric acid ion, and a thiocyanate ion.

11. A reducing process of carbon dioxide as set forth in claim 2, wherein, in the organometallic complex represented by general formula (1), the nitrogen-containing ligands represented by $X^1$ and $X^2$ are 4,4'-dimethoxy-2,2'-bipyridine.

12. A reducing process of carbon dioxide as set forth in claim 3, wherein, in the organometallic complex represented by general formula (1), the nitrogen-containing ligands represented by $X^1$ and $X^2$ are 4,4'-dimethoxy-2,2'-bipyridine.

13. A reducing process of carbon dioxide as set forth in claim 4, wherein, in the organometallic complex represented by general formula (1), the nitrogen-containing ligands represented by $X^1$ and $X^2$ are 4,4'-dimethoxy-2, 2'-bipyridine.

14. A reducing process of carbon dioxide as set forth in claim 2, wherein a pH of a reaction system mixing the organometaillic complex, carbon dioxide, and water is 6 or below.

15. A reducing process of carbon dioxide as set forth in claim 3, wherein a pH of a reaction system mixing the organometallic complex, carbon dioxide, and water is 6 or below.

16. A reducing process of carbon dioxide as set forth in. claim 4, wherein a pH of a reaction system mixing the organometallic complex, carbon dioxide, and water is 6 or below.

17. A reducing process of carbon dioxide as set forth in claim 5, wherein a pH of a reaction system mixing the organometallic complex, carbon dioxide, and water is 6 or below.

18. A reducing process of carbon dioxide as set forth in claim 2, wherein, when reducing the carbon dioxide by mixing the organometallic complex, carbon dioxide, and water, the pH of the reaction system is changed.

19. A reducing process of carbon dioxide as set forth in claim 3, wherein, when reducing the carbon dioxide by mixing the organometallic complex, carbon dioxide, and water, the pH of the reaction system is changed.

20. A reducing process of carbon dioxide as set forth in claim 4, wherein, when reducing the carbon dioxide by mixing the organometallic complex, carbon dioxide, and water, the pH of the reaction system is changed.

21. A reducing process of carbon dioxide as set forth in claim 5, wherein, when reducing the carbon dioxide by mixing the organometallic complex, carbon dioxide, and water, the pH of the reaction system is changed.

22. A reducing process of carbon dioxide as set forth in claim 6, wherein, when reducing the carbon dioxide by mixing the organometallic complex, carbon dioxide, and water, the pH of the reaction system is changed.

23. A reducing process of carbon dioxide as set forth in claim 6, comprising the steps of:
   adding hydrogen to a reaction system mixing the organometallic complex of general formula (1), carbon dioxide, and water, where the nitrogen-containing ligands represented by $X^1$ and $X^2$ are 4,4'-dimethoxy-2,2'-bipyridine; and
   applying a pressure on the reaction system.

24. A reducing process of carbon dioxide as set forth in claim 7, comprising the steps of:
   adding hydrogen to a reaction system mixing the organometallic complex of general formula (1), carbon dioxide, and water, where the nitrogen-containing ligands represented by $X^1$ and $X^2$ are 4,4'-dtmethoxy-2,2'-bipyridine; and
   applying a pressure on the reaction system.

* * * * *